US010556011B2

(12) United States Patent
Levine et al.

(10) Patent No.: US 10,556,011 B2
(45) Date of Patent: Feb. 11, 2020

(54) METHOD AND SYSTEM FOR ADDING SENSORY CONDITIONING CUES IN A PHARMACOTHERAPEUTIC REGIMEN

(71) Applicants: Joshua D. Levine, Chapel Hill, NC (US); Robert A. Levine, Guilford, CT (US)

(72) Inventors: Joshua D. Levine, Chapel Hill, NC (US); Robert A. Levine, Guilford, CT (US)

( * ) Notice: Subject to any disclaimer, the term of this patent is extended or adjusted under 35 U.S.C. 154(b) by 0 days.

(21) Appl. No.: 13/691,131

(22) Filed: Nov. 30, 2012

(65) Prior Publication Data
US 2013/0142839 A1 Jun. 6, 2013

Related U.S. Application Data

(60) Provisional application No. 61/566,386, filed on Dec. 2, 2011, provisional application No. 61/566,915, filed on Dec. 5, 2011.

(51) Int. Cl.
*A61K 45/00* (2006.01)
*A61K 9/00* (2006.01)

(52) U.S. Cl.
CPC ............ *A61K 45/00* (2013.01); *A61K 9/0056* (2013.01)

(58) Field of Classification Search
CPC .............................. A61K 45/00; A61K 9/0056
See application file for complete search history.

(56) References Cited

U.S. PATENT DOCUMENTS

| | | | |
|---|---|---|---|
| 4,807,757 A * | 2/1989 | Rappaport et al. | ........... 206/535 |
| 5,377,841 A | 1/1995 | Varon | |
| 5,760,095 A | 6/1998 | White | |
| 6,254,857 B1 | 7/2001 | Hoic et al. | |
| 6,270,783 B1 | 8/2001 | Slavtcheff et al. | |
| 6,306,412 B1 | 10/2001 | Crotty et al. | |
| 6,333,024 B1 | 12/2001 | Masters et al. | |
| 6,346,231 B1 | 2/2002 | Opheim | |
| 6,855,324 B2 | 2/2005 | Sandler | |
| 6,973,374 B2 | 12/2005 | Ader | |
| 2002/0061317 A1* | 5/2002 | Sandler | ........... 424/400 |
| 2003/0017998 A1 | 1/2003 | Snow et al. | |
| 2003/0032600 A1 | 2/2003 | Ulrich et al. | |
| 2003/0114475 A1 | 6/2003 | Fox et al. | |
| 2003/0225003 A1 | 12/2003 | Ninkov | |
| 2004/0153214 A1 | 8/2004 | Ader | |
| 2004/0166063 A1 | 8/2004 | Siegel | |
| 2004/0185093 A1 | 9/2004 | Szymczak | |
| 2005/0059698 A1* | 3/2005 | Selbo et al. | ........... 514/305 |
| 2005/0136106 A1 | 6/2005 | Sandler | |
| 2005/0152974 A1 | 7/2005 | Boehm et al. | |
| 2006/0052428 A1 | 3/2006 | Chez | |
| 2006/0068003 A1 | 3/2006 | Herz | |
| 2006/0141031 A1* | 6/2006 | Nelson et al. | ........... 424/464 |
| 2006/0142398 A1* | 6/2006 | Went | ........ A61K 31/13 514/662 |
| 2007/0231387 A1 | 10/2007 | Levi et al. | |
| 2008/0152771 A1 | 6/2008 | Scalisi et al. | |
| 2011/0311622 A1 | 12/2011 | Levine et al. | |

FOREIGN PATENT DOCUMENTS

WO    WO2008069970    *   6/2008    ........... A61K 31/465

OTHER PUBLICATIONS

Das et al., multi-functional signal modulation therapy of canc er: ancient weapon, modern targets, Mol. Cell. Biochem., 2010, vol. 336, pp. 85-95.*
Clark et al. "Scientific and Ethical Issues in the Use of Placebo Controls in Clinical Trials", Annual Review Public Health, vol. 15, 1994, pp. 19-38.
Sandler et al. "Conditioned Placebo Dose Reduction: A New Treatment in Attention-Deficit Hyperactivity Disorder?" Journal of Developmental & Behavioral Pediatrics, vol. 31, No. 5, Jun. 2010, pp. 369-375.
Ader et al. "Conditioned Pharmocotherapeutic Effects: A Preliminary Study", Psychosomatic Medicine, vol. 72, 2010, pp. 192-197.
Lidstone et al. "Effects of Expectation on Placebo-Induced Dopamine Release in Parkinson Disease", Arch Gen Psychiatry, vol. 67, n. 8, Aug. 2010, pp. 857-865.
Benedetti et al. "Conscious Expectation and Unconscious Conditioning in Analgesic, Motor, and Hormonal Placebo/Nocebo Responses", J. Neurosci., May 15, 2003, vol. 23, n. 10, pp. 4315-4323.
Chaput de Saintonge et al. "Harnestting Placebo Effects in Health Care," The Lancet, vol. 344, Oct. 8, 1994, pp. 995-998.
Voudouris et al. "The Role of Conditioning and Verbal Expectancy in the Placebo Response", Pain, vol. 43, 1990, pp. 121-128.
Schagen van Leeuwen et al. "The Placebo Effect in the Pharmacologic Treatment of Patients with Lower Urinary Tract Symptoms", European Urology, vol. 50, 2006, pp. 440-453.
Adesman, "The Diagnosis and Management of Attention-Deficit/ Hyperactivity Disorder in Pediatric Patients", Primary Care Companion J Clin Psychiatry, 33(2), 66-77, 2001.
Flaten, "Caffeine-Associated Stimuli Elicit Conditioned Responses: An Experimental Model of the Placebo Effect," Psychopharmacology, 145, 105-112, 1999.

(Continued)

*Primary Examiner* — Zohreh A Fay
(74) *Attorney, Agent, or Firm* — O'Shea Getz P.C.

(57) ABSTRACT

A method and system for administering pharmaceutical agents to a subject is provided. The system includes a course of treatment regimen, which includes a prescribed order of medicine amounts for periodic administration to the subject in the prescribed order. The amount of medicine includes a dose of at least one active pharmacological agent (APA) and an amount of at least one non-active pharmacological agent (NPA). The NPA provides at least one non-visual sensory cue. The dosage amounts of the APA contained within the amounts of medicine periodically administered in the prescribed order are varied within the course of treatment regimen, and the amount of the NPA contained within the amounts of medicine periodically administered in the prescribed order are held constant within the course of treatment regimen.

12 Claims, No Drawings

(56) References Cited

OTHER PUBLICATIONS

Grieve, M. "Mint", 1995, Botanical.com, pp. 1-22.
Office action for U.S. Appl. No. 13/141,594 dated Aug. 14, 2012.
Office action for U.S. Appl. No. 13/141,594 dated Feb. 15, 2013.
Office action for U.S. Appl. No. 13/141,594 dated Feb. 14, 2014.
Office action for U.S. Appl. No. 13/141,594 dated Sep. 5, 2014.
Office action for U.S. Appl. No. 13/141,594 dated Nov. 16, 2015.
Office action for U.S. Appl. No. 13/141,594 dated Jul. 1, 2016.

* cited by examiner

METHOD AND SYSTEM FOR ADDING SENSORY CONDITIONING CUES IN A PHARMACOTHERAPEUTIC REGIMEN

The present application is entitled to the benefit of and incorporates by reference essential subject matter disclosed in U.S. Provisional Patent Application Ser. No. 61/566,386 filed Dec. 2, 2011 and U.S. Provisional Patent Application Ser. No. 61/566,915 filed Dec. 5, 2011.

BACKGROUND OF THE INVENTION

1. Technical Field

The present invention describes a method for administering active pharmaceuticals (chemically synthesized, bioengineered, naturally occurring, or botanically derived) to a patient during a course of treatment. In particular, the present method makes use of the 'placebo response', and enhances it through the conditioning achieved by combining initial therapeutic pharmacological levels of the active pharmaceutical agent with "inactive" conditioning agents that contain a sensory cue or cues. The term "inactive" means that the agent is not known to have significant pharmacological effects or only minor effects unrelated to the effects of the APA. The term "sensory conditioning cue" refers to both conscious conditioning and/or subconscious conditioning.

BACKGROUND INFORMATION

It has been shown in numerous studies that when patients believe they are receiving a potent medication (even though the "potent" medication contained no active pharmacological ingredients) they will heal more rapidly and/or feel better more quickly and/or more fully than patients who are not given such treatment. The administration of a "placebo" (i.e., a non-active substitute for an active pharmacological agent) can activate physiological responses similar to those experienced by a patient receiving an active pharmacological agent. While the "placebo response" may not be entirely understood by modern science, it is well documented that rather than simply convincing patients into believing that they are getting better, improving, or healed, the so-called "placebo" can actually effect a scientifically documentable improvement or cure. In many studies of pharmacological efficacy the "active drug" performs only marginally better or moderately better, and in some cases no better, or worse than the placebo. Physicians must often weigh whether this small additional level of improvement is worth the concurrent risk of side effects caused by active pharmaceuticals. Placebos, by definition have little or no side effects since they are composed of substances generally recognized as safe and inactive. The use of placebos is widespread in both traditional and modern medicine and arguably form the foundation of many systems of medicine practiced around the world.

The use of non-pharmacologically active (NPA) substances to effect a cure is highly desirable for a variety of reasons, including the fact that NPAs typically: 1) have less or no side effects; 2) cost less; 3) have less or no interaction with other medications; 4) have a decreased chance of addiction; and 5) have less or no side effects and/or complications associated with usage over an indefinite time period.

There are, however, a number of difficulties presented to a doctor wishing to treat a patient with a placebo. For example, a patient who enrolls in a double-blind study will be informed that they may be given a placebo treatment as part of their participation in the study. Absent this informed consent of the possibility of taking placebos, there are potentially serious ethical dilemmas associated with a doctor telling a patient he is receiving an active pharmacological agent (APA) when he is in fact being given a placebo. This can prevent a doctor from giving a patient a placebo, thereby limiting or attenuating the potential benefit of the placebo response to the patient's health.

SUMMARY OF THE INVENTION

The current invention provides a method and system for administering an amount of medicine containing an active pharmaceutical agent and a placebo-response-evoking agent consisting of a NPA that gives a sensory cue combined in a unitary dose form with the APA. The efficacy of the NPA as an evoker of the placebo response is augmented by coupling the sensory cue containing NPA with the active pharmacologic agent, and by administering in a form that has detectable sensory effects (e.g., taste, smell, sound such as verbal communication, cutaneous sensation, oropharyngeal or esophageal/gastric somatosensory, or sensations such as warmth or coolness, etc.) thereby causing the patient consciously and/or unconsciously to associate the sensory cue with the effects of the APA. The NPA may be substances that are generally recognized as safe or GRAS agents, but any agent that is not a cause of serious untoward effects may be employed. This association, conditioning, or learning will allow the sensory cue to evoke effects similar to the APA via what is referred to as the 'placebo response' thereby permitting lower amounts of APA to be used in subsequent doses when accompanied by the placebo-response-evoking sensory cue contained in the NPA. Sensory cues that may be employed in this invention include those mentioned as well as cues derived from somatic senses including the sensations of touch, pressure, temperature, nociception (pain) and proprioception. Oropharyngeal somatosensory sensations are somatic sensations perceived in the oropharynx, the region extending from the uvula to the hyoid bone.

According to an aspect of the present invention, a method for administering pharmaceutical agents to a subject is provided. The method includes the steps of: a) providing a course of treatment for a subject, which course includes periodically administering an amount of medicine to the subject, which amount of medicine includes a dose of at least one active pharmacological agent (APA) and an amount of at least one non-active pharmacological agent (NPA), which NPA provides at least one non-visual sensory cue; and b) varying the dosage amount of the APA within the periodically administered amount of medicine (e.g., generally periodically decreasing the APA from customarily prescribed dosages to dosages below the generally prescribed dosage of the APA), while the amount of the NPA contained within each periodically administered amount of medicine is provided at a constant level that maintains the sensory cue at a substantially consistent level from dose to dose.

According to another aspect of the present invention, a system for administering pharmaceutical agents to a subject is provided. The system includes a course of treatment regimen, which includes a prescribed order of medicine amounts for periodic administration to the subject in the prescribed order. The amount of medicine includes a dose of at least one active pharmacological agent (APA) and an amount of at least one non-active pharmacological agent (NPA). The NPA provides at least one non-visual sensory cue. The dosage amounts of the APA contained within the amounts of medicine periodically administered in the prescribed order are varied within the course of treatment regimen, and the amount of the NPA contained within the amounts of medicine periodically administered in the prescribed order are held constant within the course of treatment regimen.

For many of the sensory cues that can be used under the present invention, the sensation provided by that sensory cue is preferably, but not necessarily, initially perceived by the subject about the same time as the onset of the pharmacological effect (from the APA) is noted by the subject. Most preferably, the perception of the sensory cue temporally overlaps with the pharmacological effect of the APA. The "about the same time" is used herein to mean that the two events (i.e., the perception of the sensory cue and the onset of the pharmacological effect) occur at the same time, or alternatively in temporal proximity that is close enough such that the two events can be causally linked by the subject. In some instances, a greater period of time between the perception of the sensory cue and the onset of the pharmacological effect is acceptable; e.g., a sensory cue that occurs sometime before or after the onset of the pharmacological effect has taken place.

For example, the onset of analgesia with narcotics may be some period of time (e.g., fifteen minutes to forty-five minutes) after the drug is taken. Factors that can affect the onset of the drug include the drug itself, the method of administration of the drug (e.g., oral, sublingual, transmucosal, intravenous intramuscular, subcutaneous or transdermal), or the formulation of the drug; e.g., a rapid dissolution formulation, or a formulation that delays onset, such as an enteric coated drug, or a continuous release formulation. Depending upon the known pharmacokinetics of the APA and its method of administration, the sensory cue is preferably formulated to effect its perception at or about the same time as the APA begins to be effective. As another example, consider an oral narcotic agent whose expected onset of action is about thirty minutes. The sensory cue (e.g., a taste and olfactory sensation such as cinnamon) could be provided with the narcotic agent in such a manner that it is ingested at the same time as the narcotic agent, but is not perceived by the subject until the onset of the narcotic agent. Aromatic volatile oils such as mint, ginger, *eucalyptus*, thyme, aniseed, garlic, and wintergreen are other examples of sensory cues that could be used in such a "timed" application. As yet another example, the sensory cue NPA may be contained on the exterior of a pill or capsule or in the interior core of a pill/capsule beneath a time-release delay coating so that the coating dissolves and releases the NPA at about the same time the APA is perceived as acting. As a result, the subject feels a sensation of warmth, coolness, or tingling in their upper digestive tract, or smells the absorbed aromatic volatile oil on their breath either by its presence in their blood and transmission to their expired air, or through eructation of gastric gas to the pharynx close to the time that the patient feels the effects of the APA. Any NPA having a perceived sensation may be employed. Cutaneously administered drugs, or rectal or vaginal suppositories, may include a warming, cooling, slight burning or tingling agent as the NPA sensory cue incorporated, into the cutaneous mechanism (e.g., a patch) containing the APA, formulated so that their perception occurs about the same time as the onset of the APA's physiologic response.

The duration of the sensory cue can vary to suit the application. In many instances the causal relationship between the sensory cue and the pharmacological effect of the APA is enhanced by extending the duration of the sensory cue. Typically, the duration of the sensory cue is several seconds to several minutes, although in some instances the sensory cue may be perceivable by the subject for the entire time the APA has a pharmacological effect. The specific duration can be tailored to suit the application at hand.

The term "constant" is used herein to describe, for example, that the amount of an NPA contained within each periodically administered amount of medicine is provided at a level that maintains the perception of the sensory cue(s) at a substantially consistent level and is constant from dose to dose, while the APA dose is varied and generally decreased. In that context, the term "constant" is used to mean that the amount of the NPA contained within the administered amounts of medicine, and therefore the associated sensory cue, is substantially the same within each of the administered amounts; e.g., each administered amount of medicine has the same amount of NPA in it, and consequently the perceived sensation from the sensory cue is the same in each administered amount of medicine regardless of the dosage of APA within the amount of medicine. In this context, the term "constant" does not mean that the perceivable aspect of the sensory cue (e.g., its intensity) necessarily remains the same all the time the medicine is administered. As indicated above, the sensory cue typically, but not necessarily, has a duration that is less than the pharmacological duration of the APA. For example, the APA may have a pharmacological duration that lasts a period of four hours, but the sensory cue may only last ten minutes. In those preferred applications where the onset of the pharmacological effect begins at the same time as the onset of the sensory cue and using the details of this example, the sensory cue is perceivable by the subject during the first ten minutes of the four hour APA duration period.

In some applications, it is possible that a course of treatment that included a relatively low dosage of APA over an extended period of time could result in an attenuation of the desired response from the subject; e.g., the desired association of the sensory cue to the perceived pharmacological effect of the APA can be diminished—a process sometimes referred to as "extinction". In such an event, or to prevent such an event, the present method and system can include a periodic amount of medicine that includes a greater dose of the APA than the earlier applied doses (e.g., a "spike" in APA dosage) which is followed by the resumption of the lower dose of the APA with the standard sensory cue; i.e., the resumption of the normal regimen. This aspect of the present method and system would help to prolong the efficacy of the APA in lower dose amounts and would also be advantageous to the patient in that it would more rapidly restore the conditioned physiologic response due to the "relearning" of the conditioned response initial learned under the system. This aspect of the present invention may be referred to as "intermittent reinforcement". It can be accomplished by giving a single dose of a higher APA with the sensory cue followed by resumption of the previously administered lower dose or the lowest effective dose.

In some embodiments, the physician may continue to administer the combination of the NPA and APA, with the APA at the lowest effective level for the patient and the NPA at a constant original level, thereby minimizing side effects of the APA that may be dose dependent. The APA dose level may be at any level within the generally recommended dose levels to levels that are thought to be pharmacologically inactive; the APA may be administered at a dosage that is the lowest dosage that will be effective for the patient taking the combined APA and NPA of the present invention.

One of the advantages provided by the present method is that the sensory cue(s), of perceived taste (such as that of cinnamon or chocolate), or tingling (such as that induced by *echinacea*), or sense of heat/minor burning sensation (such as that induced by capsaicin or ginger), or sense of cooling (such as that induced by menthol) associated with the APA is stronger and longer lasting and much more certain to be perceived than a visual cue. It is known in the prior art to use a placebo dose of medicine within a prescribed course of treatment. For example, U.S. Pat. No. 6,855,324 "Therapeutic Placebo Enhancement of Commonly-Used Medications" describes a method for reducing the normal dosage of a pharmaceutical that involves the use of visual indicia associated the use of a full dosage and with a placebo (e.g., "the pill marked 'XXX' is the strong one"). At a certain point in the treatment, a reduced dosage of the pharmaceutical is used with the placebo. Problems with using a visual indicia include the fact that they are only discernible prior to being ingested, they require the subject to be able to see them, and once ingested they are gone—nothing remains to reinforce the association between the visual cue and the medicine with which it is associated. Equally problematic is the fact that many medications are taken together and or administered to the patient by others and visual cues are therefore non-effective. The present invention, in contrast, uses a sensory cue that can remain with the subject for a period of time, does not rely on the subject's ability to see, and will be substantially more noticeable that a visual cue; e.g., a bitter flavor or tingling sensation can stay in the subject's mouth for a sufficient period of time to reinforce the desired association with the APA.

Another advantage of the present invention is that the present method for administering an amount of medicine capitalizes on and potentially increases the reassurance provided to a patient by his or her physician. The present coupling of a placebo with an active pharmacologic agent, which coupling generally requires a prescription or contact with his or her healthcare provider and therefore requires enhanced contact between the physician and patient, further augments the placebo response experienced by the patient. Coupling the placebo and the APA also avoids disclosure difficulties associated with a doctor wishing to treat a patient with a placebo. The co-administration of a placebo together with an APA resolves the disclosure difficulties since the patient will fact be receiving an APA. The combination described in the present invention will allow the physician to use the lowest possible dosage of APA thereby decreasing (or possibly eliminating) the dose related side effects of the APA, thereby enhancing the efficacy of the APA and or the efficacy of the placebo depending upon ones perspective. The net effect is that the patient will get the same therapeutic response from a lower dose of APA thereby reducing (or possibly eliminating) untoward effects, or side effects, of the APA.

Subjects likely to benefit by the present method include those that are taking an APA for pain, mood disorders, anxiety, high blood pressure, depression, asthma, allergies, drug dependence, addiction to nicotine, insomnia, as well as symptoms triggered by chemical sensitivities. It will also benefit many other conditions including those with a possible psychosomatic trigger such as irritable bowel syndrome, sexual dysfunction, eating disorders including obesity, back pain, and various phobias.

The present apparatus and advantages associated therewith will become more readily apparent in view of the detailed description provided below.

DETAILED DESCRIPTION OF THE INVENTION

According to the present invention, a method and system for periodically administering a medicine containing one or more active pharmaceutical agents (chemically or biologically synthesized, or botanically derived) to a patient within a prescribed course of treatment is provided. The periodically administered medicine may assume a variety of different forms (e.g., pill, capsule, tablet, powder, cream, patches, liquid, gas, etc), depending upon the application at hand. In some embodiments, the medicine may be in a form that contains a pharmaceutical agent in a form that is otherwise available to the public, which form is modified according to the present invention; e.g., a commercially available pharmaceutical pill, modified via coating or admixing to include a non-active pharmaceutical agent sensory cue. Hereinafter, the form of the medicine will be referred to hereinafter as a "pill" for ease of description. The periodically administered medicine is not, however, limited to only a solid "pill" form.

The one or more active pharmacological agents (APAs) within the pill are specifically chosen to create a desired effect on the subject taking the medicine. In addition to the APAs, each pill also includes an amount of one or more non-active pharmacological agents (NPAs). The NPAs include a composition that is, individually or collectively, capable of giving the patient a conscious (perceptible) and/or unconscious (imperceptible) cue or cues (referred to hereinafter as a "sensory cue") to its presence. A sensory cue may be perceptible immediately prior to or at the time of ingestion or application or within some period of time (e.g., thirty to forty-five minutes) after ingestion or application; e.g., cues such as smell, taste, tactile texture, mouth sensation, upper gastrointestinal sensation, and involuntary response (e.g., salivation). Sensory cues induced by stimulating the somatosensory system of the tongue and mouth include sensations such as burning, tingling, hotness, coolness, astringency, carbonation, mouthfulness (heartiness/kokumi), numbness, etc., can be particularly effective because of the response they create; e.g., one that can be stronger, longer lasting, and distinctive relative to sensory cues that a patient is likely to normally encounter. A patient having a dull sense of taste would likely readily recognize a tingling sensation.

As indicated above, the medicine administered within the course of treatment includes at least one NPA. In those embodiments including at least two NPAs, the NPAs can, for example, be selected to include a first NPA that provides a first sensory cue and a second NPA that provides a second sensory cue. The first sensory cue may be different from the second sensory cue. In some instances, the first sensory cue may be perceivable by the subject before the second sensory cue is perceivable by the subject. In other embodiments having at least two NPAs, the NPAs may each provide the same or similar sensory cue. In some of these embodiments, the sensory cue of the first NPA may be perceivable by the subject before the sensory cue of the second NPA.

In some embodiments, the effectiveness of the present medication can be enhanced by application techniques. For example, if an NPA provides a taste, or a cool or warm oropharyngeal sensory cue (e.g., cues provided by peppermint, spearmint, wintergreen, or cinnamon oils, or their synthetic analog), the sensory cue can be enhanced by advising the subject to not to eat or drink for a period of time (e.g., thirty to sixty minutes) after ingestion. The instruction to avoid eating or drinking for the period of time will help prevent washing or diluting the NPA within the subject's pharynx and esophagus and consequently the sensory cue associated therewith. Alternatively, the subject may be instructed to let the medication dissolve in their mouth without ingestion of any liquids as in the case of sublingual administration of the medication.

The NPAs that create a sensory cue also create and/or reinforce (by conscious and/or subconscious mechanisms) an association between the cue and the effect associated with the APA. In some embodiments, the association between the cue and the APA effect is created when the subject is treated with the medicine containing the APA over a period of time, and the sensory cue accompanying the APA becomes associated with the relief (i.e., effect) provided by the APA over the period of time. For example, under the present invention a pill containing a prescribed dosage of an anti-inflammatory agent could contain a specific amount of an NPA that imparts an arbitrarily chosen flavor, a mouth sensation, or has a distinct smell. After a period of time, that flavor, mouth sensation or smell will become associated with the anti-inflammatory relief provided by the APA. As a result, the subject will expect the anti-inflammatory relief, or be conditioned to experience the relief, when a pill is taken having the particular flavor, sensation, or smell.

In other embodiments, the association between the sensory cue and the APA effect is a naturally occurring one (i.e., one that is independent of the medicine) that is reinforced when the subject is treated with medicine containing the APA and a NPA that imparts a particular sensory cue. For example, a pill containing a prescribed dosage of a strong anti-inflammatory agent may contain a specific amount of an NPA that contains or mimics the flavor and mouth sensation of capsaicin (chili pepper), which flavor is associated with anti-inflammatory relief. If the NPA actually contains capsaicin, the amount of the capsaicin is less than an amount that would provide anti-inflammatory relief to the subject by itself, but is an amount that is sufficient to provide the flavor and sensation associated with capsaicin. Hence, the anti-inflammatory relief provided by the medicine is naturally associated with the taste and sensation of the capsaicin (chili pepper), but it is the APA that provides the anti-inflammatory relief—not the capsaicin sensory cue associated with the aforesaid relief. Other examples of combinations of a product having a sensory cue that is associated with particular relief and an APA that provides such relief include, but are not limited to: a) licorice or peppermint associated with an APA that restores calm breathing; b) chamomile flavor associated with an APA that helps induce sleep or calms anxiety; c) ginger, peppermint, or fennel associated with an APA that helps dissipate or prevent motion sickness; d) peppermint or chamomile associated with an APA that provides relief for irritated bowel syndrome; e) opiate alkaloids or opium-less and alkaloid-free seed poppy cultivar associated with an APA that provides pain relief; f) *Echinacea* alkymides and garlic associated with an APA that is an antiviral; g) licorice or coffee associated with an APA that provides asthma relief; h) lemon balm, chocolate, or bitters associated with an APA that provides depression relief; i) bergamot associated with an APA that provides relief for obsessive compulsive disorder; and j) chamomile or licorice associated with an APA used to treat ulcers.

For medicines that are, or were originally, directly or indirectly botanically derived, the NPA may contain non-active constituents of the plant from which it was derived. These non-active constituents, with nearly identical chemical compositions, may trigger unconscious perceptions/cues and enhance the effect of the NPA treatment regimen. For example, in certain applications an APA such as caffeine may be administered as treatment of various disorders and conditions (i.e., migraines, fatigue). In such applications, decaffeinated coffee (i.e., a non-active constituent derived from a botanical source) can provide both conscious and unconscious sensory cues that can enhance the effect of the NPA treatment regimen.

In some embodiments, a synthetically derived APA may be combined with one or more sensory cues of analogous plant medicines that produce the same pharmacological actions. For example, a synthetic opioid may taste strongly bitter and may numb the mouth like the *Papaver somniferum* alkaloid from which it was originally derived. A medication for flatulence or colic may have a fennel (*Foeniculum vulgare*) smell. A medication for ulcerative conditions of the bowels may have a peppermint smell which is known to have relaxing, anti-inflammatory effects on the muscles of the digestive system. A medicine to treat microbial infections may include the alkylamides of *Echinacea* spp. that produce a strong tingling sensation on the tongue. The sensory cues (both conscious and unconscious) assist the body in "understanding" and reacting to the medicine. They enhance the effect of the non-active pharmacological agents by providing memorable associative cues with the medication containing the active pharmacological agents.

Additional examples of sensory cues provided by an NPA include: diaphoretic/sudorific agents that increase the subject's propensity to sweat (e.g., elder flower, yarrow, cayenne/capsaicin); agents that color or add odor to the subject's urine or feces (e.g., beet juice, asparagus); aromatic volatile oils that may be sweet, spicy, and/or fragrant (e.g., cinnamon, fennel, dill, lemon balm, peppermint, spearmint, ginger, caraway, *eucalyptus*, aniseed, thyme, sage, cardamom, wintergreen, juniper, chamomile, parsley, oregano, garlic); agents that cause the subject's sweat to smell (e.g., garlic); sialagogue agents that increase the propensity of the subject to salivate (e.g., cayenne, ginger, gentian, black pepper); rubefacient agents that increase localized blood flow and warms the local area when applied to the skin (e.g., horseradish, mustard, cayenne, wintergreen, peppermint oil, rosemary oil, ginger); agents that provide a cool sensation (e.g., refrigerant herbs such as aloe, *hibiscus*, orange, lemon, coriander, licorice); agents that provide a bitter taste/mouthfeel (e.g., gentian, horehound, yarrow, mugwort, wormwood, chamomile, dandelion); astringent agents that provide a taste/mouthfeel (e.g., tea, raspberry leaf, oak, yarrow); demulcent agents that provide a mouthfeel (e.g., oat, flax, marshmallow, licorice, slipper elm, cornsilk); agents that act as a mild stimulant (e.g., chocolate, cola, tea, coffee, rosemary, peppermint); and agents that provide a sour taste (e.g., lemon, citric acid). The above is a list of acceptable sensory cue agents. The present invention is not limited to these examples, however. Other sensory cues not listed here that cause any kind of noticeable but harmless bodily sensation may be employed in the scope this invention.

In some embodiments, the NPA that creates or causes the sensory cue is admixed with the APA within a particular form; e.g., a pill, liquid, gel, etc.

In other embodiments, the NPA that creates or causes the sensory cue is provided in a form where it is not admixed with the APA. For example, the NPA could be a coating on materials that include the APA; e.g., a coating on a pill, etc. Alternatively, the NPA could be incorporated into, or coated onto a capsule that is used to contain materials including the APA. For example, it is known to use gelatin capsules to "package" medicines, which "package" can be ingested. In many instances, but not all, the gelatin capsules are purposefully non-flavored. In other instances, however, the capsules are purposely given a flavor designed to increase the palatability of the capsule. U.S. Pat. No. 6,346,231 "Flavored Gelatin Capsule and Method of Manufacture" discloses such a gelatin based capsule, and is incorporated by reference herein in its entirety. The flavor is chosen for solely for palatability purposes (e.g., to obscure unpalatable taste of fish oil), however, and there is no association with the relief provided by the APA. Under the present method, the NPA can be incorporated into, or coated onto a capsule that is then used to contain materials including the APA. One of the advantages of this approach is that different medicines that produce the same or very similar result, or variable dosages of one medication, can use the same type of capsule having a particular sensory cue. The present method is not limited to gelatin-type capsules, and can have an NPA included: 1) with the contents of the APA; 2) as a coating on an APA pill surface; 3) at the core or inside of an APA pill and surrounded by a time-released coating; 4) within a second outer capsule containing both the APA in its original form (e.g., pill) in addition to an NPA; 5) within the composition of the second capsule; or 6) as a surface coating on the second outer capsule.

In those applications wherein the NPA is incorporated into, or coated on, a capsule, that same capsule can be used to encapsulate a previously manufactured pill or capsule. In this manner, a sensory cued placebo could be readily used in a prescribed course of treatment as described herein with any APA/medication. This application provides substantial utility because the placebo sensory cue can be added by different stages in the production/administration of the medicine; e.g., added by the original manufacturer of the medication, or by a second-party company to previously manufactured medicine, or by a pharmacist filling a prescription with instructions to add a placebo cue—potentially within a course of treatment wherein the dosage of the APA is reduced over time.

Under the present method, the amount of the APAs within each periodically administered pill is varied over a prescribed course of treatment. In some embodiments, the amount of APA is decreased over a period of time. The present method is not limited, however, to embodiments wherein the amount of the APAs is decreased over time, and the amount of APA may be otherwise varied as the signs or symptoms of the illness for which it is administered vary, and as the physician or health care provider direct. For example, in some embodiments where the dosage amount of the APA within each periodically administered amount of medicine is gradually decreased over the course of treatment, the APA dosage may be increased for a single dose to reinforce the conditioning process followed by resumption of the decreased dose of the APA; e.g., if the course of treatment involves twenty amounts of medicine to be periodically administered, and the dosage amount of the APA decreases between the first application of the medicine and the tenth application of the medicine after which point the APA dosage plateaus at a decreased amount, this embodiment of the present invention involves a "spike" in APA dosage at some point during the "decreased amount plateau". The spike may be one or two APA applications at the initial dosage, followed by a return to applications of the decreased APA dosage amount.

Under the present method and system, the course of treatment regimen is operable to be administered over a period of time, and that period of time is long enough such that the subject will associate the sensory cue associated with the NPA with the pharmacological actions of the APA, thereby inducing a conditioned response based on the sensory cue, which response is similar to the APA.

The sensory cue provided (or caused by) the NPA in each pill enhances the action of the APA. As the amount of APA is gradually decreased within each pill over time, the effect of the NPA induced placebo response proportionately increases and in some cases may become the predominant healing factor. The present method is not limited to a particular manner of decreasing the APA dosage; e.g., the decrease may sigmoidal with no or minimal taper for the first several days to maximize conditioning followed by a exponential taper followed by a constant or plateau low dose of APA, or be linear, with or without a step function, decrease, etc. As the amount of APA is decreased, the sensory cue provided by the NPA contained within each pill remains substantially constant and gives the subject the impression that each pill is in fact the same. In most embodiments of the present method, the amount of the APA within each pill is decreased over time until a lower limit of APA is reached. At that point, each pill will contain the lower limit amount of APA so the subject is always taking some amount of APA during the prescribed course of treatment. The decreased dosages of the APA will very likely result in a significant decrease in APA associated side effects, such as nausea, diarrhea, metabolic disorders, and others.

An additional means of associating the sensory cue with the actions of the APA is to employ a multi-layered, time-delayed release dose of medication wherein the sensory cue is released in temporal proximity with the perceived action of the APA more than once in a given administered dose. This 'teaching dose' may be employed in topical patches, or in delayed release oral medications, or some combination thereof. For example, the APA and the NPA within each periodically administered medicine amount may be administered in a layered arrangement having layers of NPA and APA so that sub-amounts of the NPA and APA within the medicine amount are sequentially released thereby enhancing the associative reinforcements. Additional methods, known to those skilled in the technology, may include encapsulated granules of NPA and APA so composed as to sequentially release at about the same time in one episode or a series of episodes after the ingestion or application of a single dose. The layering of the NPA refers to both physical layering and/or temporal layering so that the release of the NPA and APA may be coordinated to best affect a conditioning association between the sensory cue and the effects of the APA.

In the aforementioned manner, patients taking the prescribed medicine can benefit from both the pharmacological action of the APA and the enhanced "placebo effect" of the NPA. The NPA placebo effect will be enhanced because it is associated (both consciously and unconsciously) with a true pharmacologic effect. The physician may prescribe a medication course of treatment wherein the amount of APA tapers down (e.g., "x" percent decrease per day) with no change in the number of pills prescribed each day. Maintaining the prescription at a fixed number of pills likely decreases the potential for medication dosing errors; e.g., applications where the amount of APA is decreased by decreasing the number of pills taken, leading to errors in the number of pills to be taken. In many instances, the patient can continue to take the medication containing the lowest dose of APA to which the disorder being treated is responsive. Maintaining the APA at a very low dose (but still requiring a prescription) also provides the psychological advantage of the subject being under a doctor's supervision and thereby enhancing the salutary effect of the doctor patient interaction and strengthening the placebo response. The supervision helps reinforce the expectation that the course of treatment is significant in providing relief. In other embodiments, the amount of APA within each periodically administered amount of medicine is below the lowest dose with a known pharmacological effect, in which case the dosage of APA may be considered to be a non-active amount of the APA.

The present method for periodically administering a medicine containing one or more active pharmaceutical agents to a patient within a prescribed course of treatment utilizes packaging that facilitates the administration of the medicine. For example, the medicine can be dispensed using a blister pack, or other sequence noting dispenser that makes clear the sequence of pills administered to date. This type of packaging is particularly useful for those applications wherein the pills containing the varying levels of APA and constant levels of NPA are visually identical or difficult to differentiate from each other.

Although the invention has been described and illustrated with respect to exemplary embodiments thereof, the foregoing and various other additions and omissions may be made therein and thereto without departing from the spirit and scope of the present invention.

What is claimed is:

1. An opioid administration kit, comprising:
   a sequential order of medicine amounts, wherein each said medicine amount in the sequential order is in a unitary form and includes a dose of at least one opioid and an amount of at least one non-active pharmacological agent (NPA), wherein the amount of NPA is configured to provide at least one non-visual sensory cue; and
   wherein the opioid dose in each medicine amount within the sequential order is greater than the dose of opioid contained within the next medicine amount within the sequential order, and each medicine amount in the sequential order contains substantially the same amount of the NPA, and wherein the opioid dose in each medicine amount is a prescription drug; and
   packaging configured to hold the medicine amounts and indicate the sequential order of the medicine amounts.

2. The kit of claim 1, wherein the at least one opioid is a synthetic opioid.

3. The kit of claim 1, wherein the at least one NPA is configured to provide a bitter taste as said non-visual sensory cue.

4. The kit of claim 1, wherein the dose of opioid is configured to produce a pharmacological effect, and the amount of NPA is configured to begin producing the at least one non-visual sensory cue at about the same time as an onset of the pharmacological effect of the opioid.

5. The kit of claim 4, wherein the NPA is configured in a time-release form.

6. The kit of claim 1, wherein the dose of opioid is configured to produce a pharmacological effect, and each medicine amount is configured to delay the amount of NPA producing the at least one non-visual sensory cue until about the same time as an onset of the pharmacological effect of the opioid.

7. The kit of claim 6, wherein the NPA within each medicine amount is encapsulated with a coating configured to dissolve a period of time after being ingested.

8. The kit of claim 6, wherein each medicine amount is configured in a layered arrangement with at least one layer of the dose of opioid and at least one layer of the amount of NPA, and the layered arrangement is configured to cause the dose of opioid and the amount of NPA to be sequentially released after being ingested.

9. The kit of claim 6, wherein the dose of opioid in each medicine amount is disposed in a plurality first encapsulated granules, and the amount of NPA in each medicine amount is disposed in a plurality of second encapsulated granules, and the first encapsulated granules and second encapsulated granules are configured so that the amount of NPA produces the at least one non-visual sensory cue at about the same time as an onset of the pharmacological effect of the dose of opioid after being ingested.

10. The kit of claim 1, wherein the at least one non-visual sensory cue provided by the amount of said NPA is a somatosensory type sensory cue.

11. The kit of claim 1, wherein the sequential order of medicine amounts includes a spike medicine amount having a spike opioid dose, the spike opioid dose being greater than the opioid dose in the immediately previous medicine amount within the sequential order.

12. The kit of claim 1, wherein the sequential order of medicine amounts includes at least two sequential medicine amounts having the same opioid dose.

* * * * *